(12) United States Patent
Workman

(10) Patent No.: US 7,694,580 B2
(45) Date of Patent: Apr. 13, 2010

(54) BIODEGRADABLE TEST CYLINDER MOLD

(75) Inventor: Gary Workman, Lombard, IL (US)

(73) Assignee: Deslauriers, Inc., LaGrange Park, IL (US)

( * ) Notice: Subject to any disclaimer, the term of this patent is extended or adjusted under 35 U.S.C. 154(b) by 100 days.

(21) Appl. No.: 12/006,548

(22) Filed: Jan. 3, 2008

(65) Prior Publication Data
US 2009/0173163 A1    Jul. 9, 2009

(51) Int. Cl.
*G01N 3/00* (2006.01)
(52) U.S. Cl. .......................................... 73/803; 73/760
(58) Field of Classification Search ............ 73/760–803
See application file for complete search history.

(56) References Cited
U.S. PATENT DOCUMENTS

| | | | |
|---|---|---|---|
| 4,534,225 A * | 8/1985 | Peacock et al. ............... | 73/860 |
| 5,029,710 A | 7/1991 | Workman et al. | |
| 5,240,225 A | 8/1993 | Workman et al. | |
| 5,602,188 A * | 2/1997 | Nakanishi ..................... | 521/82 |
| 5,664,705 A * | 9/1997 | Stolper ........................ | 222/212 |
| 5,677,495 A * | 10/1997 | Johnson et al. ............... | 73/856 |
| 5,916,584 A * | 6/1999 | O'Donoghue et al. ....... | 424/426 |
| 6,057,137 A * | 5/2000 | Tranquillo et al. .......... | 435/174 |
| 6,354,433 B1 * | 3/2002 | Mattes ........................ | 206/228 |
| 6,923,070 B2 * | 8/2005 | Workman .................... | 73/803 |
| 6,991,408 B2 * | 1/2006 | Bottriell et al. .......... | 405/302.7 |
| 2003/0188591 A1 * | 10/2003 | Workman .................... | 73/866 |

* cited by examiner

*Primary Examiner*—Max Noori
(74) *Attorney, Agent, or Firm*—Wood, Phillips, Katz, Clark & Mortimer

(57) ABSTRACT

A biodegradable test cylinder mold is used for testing concrete specimens. The mold comprises a cylindrical wall connected to a bottom wall to define a hollow, unitary cylindrical container for receiving concrete to form a test specimen. The cylindrical container is formed of a biodegradable material comprising corn starch or a blend of corn starch and plastic.

19 Claims, 2 Drawing Sheets

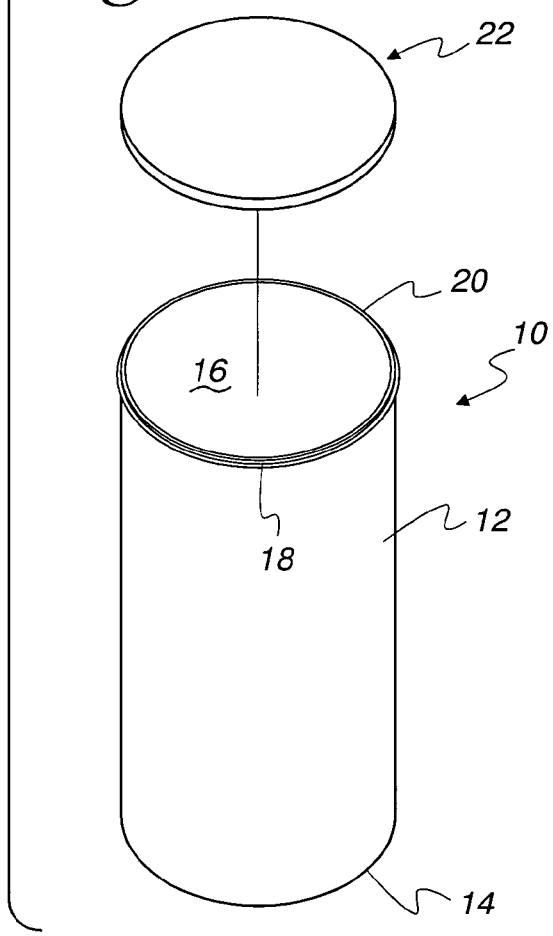
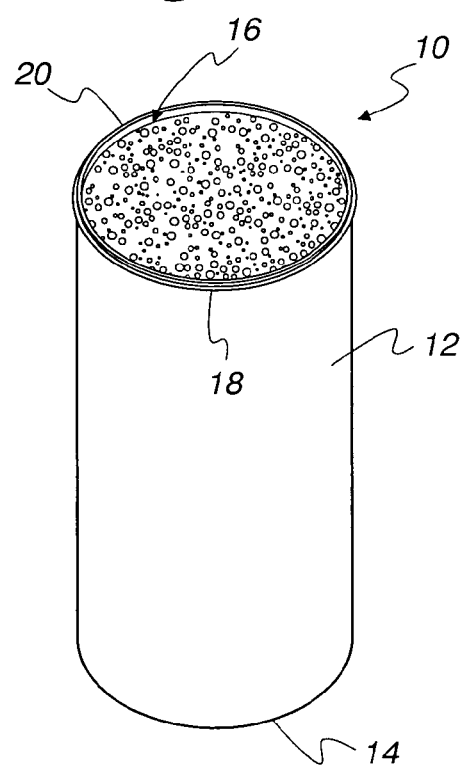
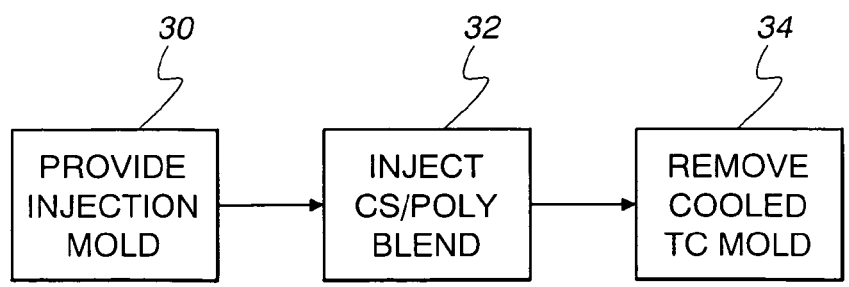

BIODEGRADABLE TEST CYLINDER MOLD

CROSS REFERENCE TO RELATED APPLICATIONS

There are no related applications.

FIELD OF THE INVENTION

This invention relates to a test center mold for testing of concrete samples and, more particularly, to a biodegradable test cylinder mold.

BACKGROUND OF THE INVENTION

Various tests have been developed to ensure that concrete used in particular applications satisfy specifications. One of these is a compression test for testing concrete cylinders. The concrete cylinder is typically formed using a test cylinder mold. The mold is a hollow cylindrical container including a bottom wall used to test specimens of concrete at a construction site. Such molds are generally disposable.

Particularly, samples of concrete are routinely acquired from job site projects for laboratory testing to verify and certify the strength of the concrete used in a specific project. The specimens are collected, according to strict ASTM guidelines, in plastic containers or wax impregnated paper cylinders, commonly referred to as concrete test cylinder molds. The test cylinder molds are offered in different sizes, such as 6 inch diameter by 12 inches high, 4 inch diameter by 8 inches high, 3 inch diameter by 6 inches high, and 2 inch diameter by 4 inches high.

Initially, such molds were made of paper board with metal bottoms. More recently, the molds are injection molded from polypropylene which is recyclable.

Reprocessors/recyclers of plastics need to know the composition of the plastic in order to sell it in the plastic material after market. For example, plastic items molded for use in the food and medical market must be molded from "virgin" material. Scrap from these processes are sold to reprocessors since the molder cannot reuse. The reprocessor knows the exact composition of the plastic material purchased from the molder and can offer it in the after market.

In a consumer recycling program, plastic items are collected in bins by the local waste company and taken to a sorting point where the recyclable materials are separated. However, there are thousands of different grades of polypropylene. The grade used for typical test cylinder molds is a copolymer, 8-10 melt, 2.5-2.7 izod material. Polypropylenes which are homo polymers have higher or lower melts, or are of different izods and cannot be used. Since the recycle symbol does not distinguish the differences in the polypropylene grades, it is doubtful the test cylinder mold material would be accepted by a reprocessor for the material after market. As a result, the molds often end up in a landfill.

Testing laboratories would be in the industrial waste management market. They would use a 20-40 cubic foot container. The plastic test cylinders would be removed from the concrete specimens and thrown into the waste container, along with the broken concrete specimens as a result of the destructive testing. As a result, most test cylinder molds wind up in landfill and can contribute to environmental problems.

In accordance with the invention, a test cylinder mold is injection molded from a biodegradable material.

SUMMARY OF THE INVENTION

In accordance with the invention, there is provided a biodegradable test cylinder mold for testing concrete specimens. The mold comprises a cylindrical wall connected to a bottom wall to define a hollow, unitary cylindrical container for receiving concrete to form a test specimen. The cylindrical container is formed of a biodegradable material comprising corn starch.

It is a feature of the invention that the cylindrical container is formed solely from corn starch.

It is another feature of the invention that the cylindrical container comprises an injection molded container.

It is a further feature of the invention that the cylindrical container is formed from a blend of corn starch and polypropylene. The blend may be approximately 40% corn starch and 60% propylene. Alternatively, the blend may be approximately one-third corn starch and two-thirds polypropylene.

It is yet another feature of the invention that the cylindrical container has a wall thickness of about 0.070 inches.

In accordance with another aspect of the invention, there is disclosed the method of forming a biodegradable test cylinder mold for testing concrete specimens, comprising: utilizing an injection molding process to form a cylindrical wall connected to a bottom wall to define a hollow, unitary cylindrical container for receiving concrete to form a test specimen, the cylindrical container being formed by injection molding a biodegradable material comprising corn starch.

Further features and advantages of the invention will be readily apparent from the specification and from the drawings.

BRIEF DESCRIPTION OF THE DRAWINGS

FIG. 1 is a perspective view of a biodegradable test cylinder mold in accordance with the invention;

FIG. 2 is a perspective view similar to FIG. 1 showing the mold filled with a concrete sample;

FIG. 5 is a flow diagram illustrating a method of forming a biodegradable test cylinder mold in accordance with the invention.

DETAILED DESCRIPTION OF THE INVENTION

Figure 3:
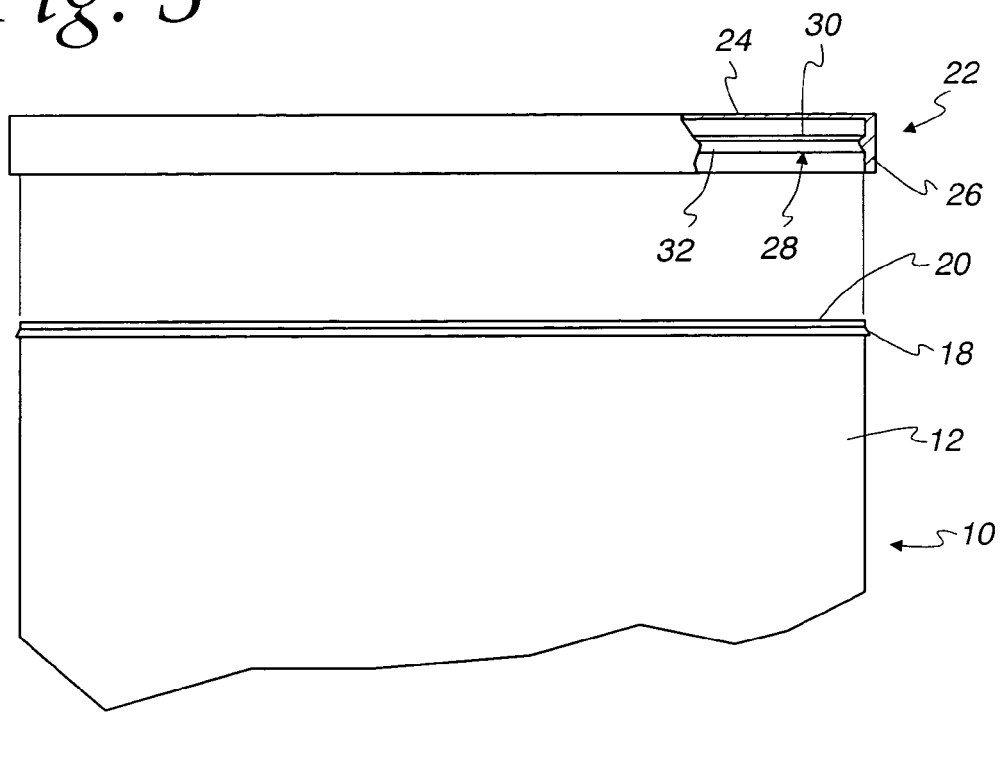
FIG. 3 is an elevation view of the biodegradable test cylinder and a removable lid.

With reference to the drawing, particularly FIG. 1, a biodegradable test cylinder mold 10 is illustrated. The test cylinder mold 10 is of one piece construction and is formed of a biodegradable material, as described below.

The test cylinder mold comprises a cylindrical wall 12 connected to a circular bottom or end wall 14 to define a hollow interior space 16. An annular ridge 18 surrounds the cylindrical wall just below a top edge 20. As such, the test cylinder mold 10 comprises a cylindrical container for receiving a sample of concrete, see FIG. 2, to form a test specimen C.

A lid 22 is removably receivable on the mold 10. Particularly, after the concrete C is placed into the mold 10, the lid 22 is used to cover the mold 10 to prevent moisture loss. Advantageously, the lid 22 is also formed of a biodegradable material.

The test cylinder mold 10 is used to collect test specimens C of concrete at a construction site. The specimen C is removed from the mold 10, often destroying the mold, and is then subject to a compression test for testing concrete cylinders. The mold 10 is then typically disposed of.

Particularly, samples of concrete are routinely acquired from job site projects for laboratory testing to verify and certify the strength of the concrete used in a specific project. The specimens are collected, according to strict ASTM guidelines, in the concrete test cylinder mold 10.

The test cylinder mold 10 has a uniform wall thickness of about 0.070 inches. The test cylinder mold 10 may be provided in different sizes, including 6 inch diameter by 12 inches high, 4 inch diameter by 8 inches high, 3 inch diameter by 6 inches high and 2 inch diameter by 4 inches high.

Referring to FIG. 3, the lid 22 comprises a top wall 24 surrounded by a short cylindrical wall 26. The lid cylindrical wall 26 has an inner diameter slightly greater than an outer diameter of the mold cylindrical wall 12. An annular locking flange 28 extends around the lid cylindrical wall 26 and has an upper shoulder 30 extending from an angled wall 32. Particularly, when the lid 22 is placed atop the mold 10, the angled wall 32 facilitates movement of the lid 22 past the ridge 18. The shoulder 30 then engages the undersigned of the ridge 18 to lock the lid 22 in place on the mold 10.

Figure 4:
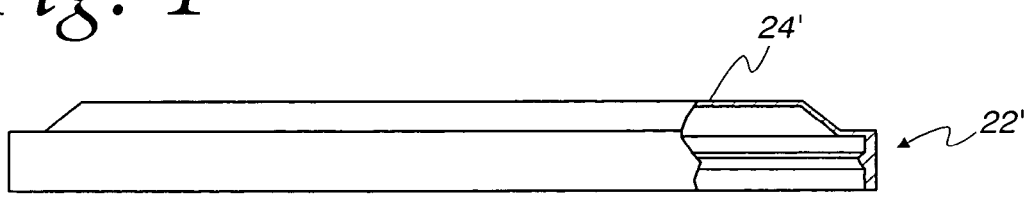
FIG. 4 is a partial sectional elevation view of a domed lid in accordance with the invention.

FIG. 4 illustrates a lid 22' which differs from the lid 22 in using a domed upper wall 24'. In all other respects, the lid 22' is similar to the lid 22. Each of the lids 22 and 22' also has a uniform wall thickness of about 0.070 inches. The size of the lid is otherwise determined by the size of the mold with which it will be used, as is apparent.

FIG. 5 illustrates a process for forming the test cylinder mold 10 of FIG. 1. The process begins at a block 30 relating to providing an injection mold. In accordance with the invention, the test cylinder mold 10 is formed by injection molding. A biodegradable material is injected into the injection mold at a block 32. The cooled test cylinder mold is then removed at a block 34. A similar process is used for the lids 22 and 22'.

A typical injection molding operation, such as for polypropylene, heats plastic pellets to approximately 450 degrees to liquify the plastic which is then forced through a nozzle into a mold. The injection mold contains the configuration of the part to be molded and is usually maintained at a temperature around 45 to 55 degrees to force the plastic to solidify. Once the part is cooled sufficiently, the injection mold opens and the molded part falls from the mold. Because of the average wall thickness of about 0.070 inches, the polypropylene must be heated to a high temperature to make it sufficiently liquid to allow it to flow the 10 to 16 inches needed to fill the injection mold before it cools to form the finished part.

In accordance with the invention, the test cylinder mold 10 and lids 22 and 22' are formed of 100% corn starch or a blend of polypropylene and corn starch. Moldable corn starch is organic and will burn and degrade at high temperatures and has a consistency similar to dough. The corn starch, alone or as blended with the polypropylene, must be at a high enough temperature to allow the material to flow without causing the corn material to burn and degrade. Also, the mold temperature must be maintained at approximately 200 degrees to allow the material to flow through the thin wall.

In accordance with the invention, the biodegradable test cylinder mold 10 and lids 22 and 22' have an izod range of 2.0 to 4.0 and a melt index of 6.0 to 14.0 with corn starch in blends from 99% polypropylene and 1% corn starch all the way up to 100% corn starch. In accordance with one embodiment of the invention, the test cylinder mold is 100% corn starch so that it is completely biodegradable.

Moreover, since 100% corn starch can be incinerated with no toxic fumes, the test cylinder can be formed of 100% corn starch for those areas which utilize incineration rather than landfills.

Advantageously, in accordance with another embodiment of the invention, the use of a blend would use about 40% corn starch and 60% polypropylene or more generally one-third corn starch and two-thirds polypropylene to satisfy requirements for "green" products. Thus, the resulting test cylinder mold and lids would be biodegradable, recyclable and capable of being molded from both reprocessed and virgin polypropylene.

Alternatively, a blend could use corn starch and other plastic materials such as polyethylene.

While the use of a biodegradable material is described herein in connection with a test cylinder mold and related lids, the biodegradable material could be used with other molded concrete forming products of similar construction. For example, a generally cylindrical sleeve of biodegradable material can also be used for forming holes through poured concrete walls.

Thus, in accordance with the invention, a biodegradable material such as a corn starch based material is used to mold a long thin walled test cylinder mold. The test cylinder mold can be considered a "green" product since disposal in the landfill will cause the product to be attacked by bacteria and slowly disintegrate into a fine powder.

I claim:

1. A biodegradable test cylinder mold for testing concrete specimens, comprising:
    a cylindrical wall having a diameter in a range of 2" to 6" and a height in a range of 4" to 12" connected to a bottom wall to define a hollow, unitary cylindrical container for receiving concrete to form a test specimen, the container having a wall thickness of at least about 0.07", the cylindrical container being formed of a biodegradable material comprising at least ⅓ corn starch.

2. The biodegradable test cylinder mold of claim 1 wherein the cylindrical container is formed solely from corn starch.

3. The biodegradable test cylinder mold of claim 1 wherein the cylindrical container comprises an injection molded container.

4. The biodegradable test cylinder mold of claim 1 wherein the cylindrical container is formed from a blend of corn starch and polypropylene.

5. The biodegradable test cylinder mold of claim 1 wherein the blend is approximately 40% corn starch and 60% polypropylene.

6. The biodegradable test cylinder mold of claim 1 wherein the blend is approximately ⅓ corn starch and ⅔ polypropylene.

7. The biodegradable test cylinder mold of claim 1 further comprising a lid formed of a biodegradable material removably receivable on the cylindrical wall to selectively close the test cylinder mold.

8. The biodegradable test cylinder mold of claim 7 wherein the lid has a domed top wall.

9. The method of forming a biodegradable test cylinder mold for testing concrete specimens, comprising:
    utilizing an injection molding process to form a cylindrical wall having a diameter in a range of 2" to 6" and a height in a range of 4" to 12" connected to a bottom wall to define a hollow, unitary cylindrical container for receiving concrete to form a test specimen, the container having a wall thickness of at least about 0.07", the cylindrical container being formed by injection molding a biodegradable material comprising at least ⅓ corn starch.

10. The method of forming a biodegradable test cylinder mold of claim 9 wherein the cylindrical container is formed solely from corn starch.

11. The method of forming a biodegradable test cylinder mold of claim 9 wherein the cylindrical container is formed from a blend of corn starch and polypropylene.

12. The method of forming a biodegradable test cylinder mold of claim 9 wherein the injection molding process is performed with a mold temperature of at least 200 EF.

13. A biodegradable concrete forming product, comprising:
an elongate, generally cylindrical wall, having a diameter in a range of 2" to 6" and a height in a range of 4" to 12",closed by a unitary end wall to define a hollow, generally cylindrical container of a select size for forming concrete, the container having a wall thickness of at least about 0.07", the generally cylindrical container being formed of a biodegradable material comprising at least ⅓ corn starch.

14. The biodegradable concrete forming product of claim 13 wherein the cylindrical container is formed solely from corn starch.

15. The biodegradable concrete forming product of claim 13 wherein the generally cylindrical container comprises an injection molded container.

16. The biodegradable concrete forming product of claim 13 wherein the generally cylindrical container is formed from a blend of corn starch and polypropylene.

17. The biodegradable concrete forming product of claim 13 wherein the blend is approximately 40% corn starch and 60% polypropylene.

18. The biodegradable concrete forming product of claim 13 wherein the blend is approximately ⅓ corn starch and ⅔ polypropylene.

19. The biodegradable concrete forming product of claim 13 wherein the generally cylindrical container is formed from a blend of corn starch and polyethylene.

* * * * *